United States Patent [19]
Chen et al.

[11] Patent Number: 6,156,346
[45] Date of Patent: Dec. 5, 2000

[54] UREASE-RESPONSIVE DELIVERY SYSTEMS FOR DIAGNOSTIC AND THERAPEUTIC APPLICATIONS

[75] Inventors: Xiaoru Chen, Pullman, Wash.; P. Jay Pasricha, Galveston, Tex.; Kam W. Leong, Baltimore, Md.

[73] Assignee: Johns Hopkins University, Baltimore, Md.

[21] Appl. No.: 09/015,502

[22] Filed: Jan. 29, 1998

Related U.S. Application Data

[60] Provisional application No. 60/036,565, Jan. 29, 1997.

[51] Int. Cl.$^7$ .............................. A61K 9/14; A61K 9/50
[52] U.S. Cl. ................... 424/489; 424/499; 424/492; 424/456; 424/486; 424/487; 424/488; 424/9.1; 424/9.2; 435/4; 435/12; 514/152; 514/198
[58] Field of Search ..................... 424/9.1, 9.2, 9.52, 424/456, 492, 60, 486, 487, 488, 489, 490; 435/12, 4; 514/152, 198

[56] References Cited

U.S. PATENT DOCUMENTS

| | | |
|---|---|---|
| 4,947,861 | 8/1990 | Hamilton . |
| 5,439,801 | 8/1995 | Jackson . |
| 5,542,419 | 8/1996 | Moulton-Barrett et al. ............ 128/630 |
| 5,686,113 | 11/1997 | Speaker et al. ......................... 424/490 |

OTHER PUBLICATIONS

Zhao et al, J. Am. Chem. Soc; 112, 6627–6634, 1990.

Morrison & Boyd, Allyn and Bacon, Inc. Organic Chemistry fifth edditon, Chapter 23, p. 887, 1981.

Walsh et al, N Eng J Med; 333: 984–991, 1995.

Pawlak, D et al, Polish Journal of Chemistry; 68: 1067–1069, 1994.

*Primary Examiner*—Diana Dudash
*Assistant Examiner*—S Sharareh
*Attorney, Agent, or Firm*—Pillsbury Madison & Sutro LLP

[57] ABSTRACT

A delivery system that releases a diagnostic marker or therapeutic agent in a manner sensitive to the concentration of urease in a physiological compartment, particularly the gastrointestinal tract, and methods of use.

5 Claims, No Drawings

UREASE-RESPONSIVE DELIVERY SYSTEMS FOR DIAGNOSTIC AND THERAPEUTIC APPLICATIONS

This application claims benefit of provisional application 60/036,565, filed Jan. 29, 1997.

BACKGROUND OF THE INVENTION

1. Field of the Invention

This invention relates to a delivery system that releases a diagnostic marker or therapeutic agent in a manner sensitive to the concentration of urease in a physiological compartment, particularly the gastrointestinal tract.

2. Background Information

*Helicobacter pylori* (previously known as *Campylobacter pylori*) has been shown to be etiologically associated with gastritis, duodenitis, gastric and duodenal ulcers (Dooley, CP. Background and historical considerations of *Helicobacter pylori*. Gastroenterol. Clin. North Am. 1993;22:1–4). Patients with these conditions may not be cured unless the organism is eliminated, usually by the use of a combination of antibiotics (Tytgat et al. *Helicobacter pylori* infection ad duodenal ulcer disease, Gastroenterol. Clin. North Am., 1993;22:127–140). Therefore, there is a need for a simple and reliable marker for *Helicobacter pylori* infection so that it can be easily diagnosed and the response to therapy be readily evaluated.

At present the most commonly used method for detecting the presence of *Helicobacter pylori* is by placing a flexible tube with a light into the patient's stomach (a procedure called endoscopy) and obtaining biopsy samples of the stomach. The samples are then cultured as well as examined histologically to look for *Helicobacter pylori*. This method is expensive, and in addition, places the patient at risk for complications from the endoscopy (Chodos et al. *Campylobacter pylori* and Gastroduodenal Disease: A Prospective Endoscopic Study and Comparison of Diagnostic tests. Am. J. Gastroenterol. 988;83:1226–1230). Noninvasive tests therefore have been developed to overcome some of these problems. One of these is a serological antibody test which measures the blood level of IgG antibody to *Helicobacter pylori*. The antibody level becomes elevated in response in *Helicobacter pylori* infection. However, a major limitation of this test is that antibody may persist in the blood even after elimination of the organism. This test is therefore not useful for determining response to therapy and cannot distinguish active infection from infection in the remote past (Brown et al, Diagnosis of *Helicobacter Pylori* Infection. Gastroenterology Clinics of N. Am. 1993;22:105–115).

U.S. Pat. No. 4,830,010 (Marshall) discusses another noninvasive test for the diagnosis of *Helicobacter pylori* that relies on the measurement of carbon dioxide ($CO_2$) in the breath. This test is based on the fact that the bacteria possesses the enzyme called urease, which breaks down urea into $CO_2$ and ammonia. To perform this test, urea, labeled with either $^{13}C$ or $^{14}C$, is orally ingested by the patient. Subsequently, breath samples are collected at 30 and 60 minutes. The orally ingested urea is broken down to $CO_2$ and ammonia by the bacteria in the stomach. $CO_2$ is rapidly absorbed into the blood and then excreted via the breath. The method used for measurement of this $CO_2$ in the breath depends on the initial labeling of the urea. If $^{13}C$-urea (nonradioactive) is used, $^{13}CO_2$ concentration in the expired breath is measured by gas isotope spectrometry (Brown et al, Diagnosis of *Helicobacter Pylori* Infection. Gastroenterology Clinics of N. Am. 1993;22:105–115). Use of $^{14}C$-urea results in the production of radioactive $^{14}CO_2$ which is measured in the breath using a scintillation counter. Both methods share a common disadvantage in that they require specially trained individuals to administer the test and special breath collection devices, and patients may have to follow potentially unwieldy instructions.

In addition to the general drawbacks associated with breath tests, each of the two breath tests has its own unique problems. The use of $^{14}C$-urea requires that radioactive material be administered to the patient. The material is expensive and a scintillation counter is required for analysis (Brown et al., Diagnosis of *Helicobacter Pylori* Infection. Gastroenterology Clinics of N.Am 1993;22:105–115; Graham, What you should know about the methods, problems, interpretations, and uses of urea breath tests. Am. J. Gastroenterol. 1991;86:1118–1122).

The use $^{13}C$-urea has the disadvantage that the detection of $^{13}CO_2$ requires a mass spectrometer, an instrument that is expensive and is not readily available in all parts of the world.

A variation on the above theme involves the detection of $^{13}C$-bicarbonate in the serum after ingestion of $^{13}C$-labeled urea (Moulton-Barret et al. Serum $^{13}C$-Bicarbonate in the assessment of gastric *Helicobacter pylori* urease activity. Am. J. Gastroenterol. 1993;88:369–74). This method is based on the fact that the $^{13}CO_2$ produced by the action of urease on $^{13}C$-labeled urea is present in the blood in the form of bicarbonate formed as a result of a reversible reaction with water:

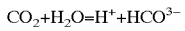

$$CO_2 + H_2O = H^+ + HCO_3^-$$

However, this method is technically demanding and, in addition, bicarbonate levels in the serum may fluctuate in response to many variables such as the acid-base balance in the blood.

The known ability of *Helicobacter pylori* to split urea is the basis for yet another test, one which requires the use of biopsy samples obtained at endoscopy. For this test, a biopsy is obtained from the patient's stomach and the specimen tested for the presence of urease (Thillainayagam et al: A Novel Enzyme Radioimmunoassay for Serodiagnosis of *Helicobacter Pylori* Infection. Gut 1991;32:467–469). Although this method gives rapid results, the requirement for endoscopy to obtain the biopsy samples is a major drawback.

Most of the above tests for *Helicobacter pylori* have mainly concentrated on the production of $CO_2$ by the action of urease on ingested urea. In contrast, there are fewer reports on the detection of ammonia which is generated along with $CO_2$ in the same reaction (Urea$\rightarrow CO_2 + 2NH_3$). Marshall has patented a method for detection of *Helicobacter pylori* by the measurement of either $CO_2$ or ammonia in the breath after a urea meal (U.S. Pat. No. 4,830,010). Other workers have shown that urine testing for $^{15}N$-ammonia after ingestion of $^{15}N$-urea is useful in the detection of *Helicobacter pylori* (Jicong et al. $^{15}NH_4^+$ excretion test: a new method for detection of *Helicobacter pylori* infection. J. Clin. Microbiol. 1992;30:181–84). Hamilton has described a method for detection of ammonia in the breath after ingestion of unlabeled urea (U.S. Pat. No. 4,947,861). This method is based on the premise that a substantial fraction of absorbed ammonia escapes metabolism by the liver (to urea) and therefore can be measured in the breath. Quite apart from the fact that this premise is not well supported by our current understanding of normal physiology, this method has the drawback of requiring a cumbersome apparatus for collection and analysis of breath ammonia.

All prior art methods focused on what until now was the only previously known target for urease reaction, mainly urea and its breakdown products i.e. $CO_2$ (detection in the breath) and ammonia (detection in the breath or urine) In contrast, the present inventors have discovered other hitherto unknown substrates for the enzyme urease which yield derivatives that can be detected in the blood or urine and serve as unique diagnostic markers for the infection.

SUMMARY OF THE INVENTION

The present invention provides novel compositions and methods for diagnosing the presence of *Helicobacter pylori* infections of the stomach or duodenum in humans or other mammals. The invention provides a urease responsive system for the delivery of diagnostic marker or therapeutic compound.

In one embodiment, the system comprises a microsphere which is stabilized by a urease sensitive cross-linker. When the cross-linker is cleaved by urease, the microsphere decomposes and the diagnostic marker or therapeutic compound is released. In a preferred embodiment, the microsphere is a gelatin composition, but it may also be formulated from other biocompatible hydrogels or water soluble polymers which can be cross linked by a urease-sensitive compound.

In another embodiment, the system comprises a carrier to whose surface a diagnostic marker or therapeutic compound is covalently bound by a urease sensitive bond. The carrier can be in the form of a microsphere or thin film of a polymeric compound or other material, so long as it is of a chemical composition which can be covalently bound by a urease sensitive bond to the diagnostic marker or therapeutic compound. The carriers can be composed of polymers used for drug delivery, such as gelatin or bovine serum albumin microspheres. The carriers can also be made of ion-exchange resins used clinically for bile acid absorption.

The term "microsphere" as used herein, is intended to mean a spherical particle in the size range of 1 to 2000 microns, and is typically composed of polymers used clinically.

In still another embodiment, the system comprises a pair of dipeptides which are linked via their amino groups by a urea bond. The term "dipeptide", as used herein, is intended to mean a diamino acid composed of any combination of the 20 natural amino acids existing in the body as well as any non-toxic amino acids and includes, for example gly-gly, gly-leu, leu-tyr, etc. In the presence of urease, the dimer is decomposed to yield free dipeptides. The dipeptides in a pair are not necessarily identical. Preferably one of the two amino acids in the dipeptide is a glycine.

The term "diagnostic marker", as used herein, is intended to mean any compound that is commonly used in a clinical chemistry laboratory or a compound that is used as a marker in a commercial diagnostic kit. Diagnostic markers to be used according to the invention include, for example p-aminobenzoic acid.

The term "therapeutic compound", as used herein, is intended to mean a drug having a therapeutic effect against gastrointestinal disease. Therapeutic compounds which can be used according to the invention include, for example, antibiotics, cytokines, and anti-inflammatory agents.

The methods of the invention can also be used to couple antibiotics via a urease-sensitive bond to an inert carrier which allows for release of the antibiotics in the stomach only in the presence of the enzyme urease. This will result in release of active antibiotic only if *Helicobacter pylori* infection is present and will minimize the incidence of adverse effects. Carriers which can be used for this purpose include, but are not limited to gelatin microspheres, geltin/chondroitin sulfate microspheres, and chitosan/alginate microspheres. Drugs which can be used for this composition and method include, but are not limited to clarithromycin, omeprazole, amoxycillin, tetracycline, and metronidazole.

In summary, it is an object of the invention to provide a composition for delivery of a diagnostic marker or therapeutic compound, said composition comprising a compound containing a urease sensitive bond.

In a preferred embodiment, the composition is a microsphere stabilized by a urease sensitive cross-linker. This microsphere may, for example, comprise gelatin.

In another preferred embodiment, the composition is a carrier which has conjugated to its surface via a urease sensitive bond said diagnostic marker or therapeutic compound. Such a carrier may be in the form of a microsphere. In a particularly preferred embodiment, the microsphere comprises poly(acrylic acid 6-aminohexylamide) beads and the diagnostic marker comprises p-aminobenzoic acid. Therapeutic compounds which are useful include omeprazole, amoxycillin, tetracycline or metronidazole.

In still another preferred embodiment, the composition comprises a pair of dipeptides linked via their amino groups by a urease sensitive bond. In a particularly preferred embodiment, the pair of dipeptides is represented by the formula.

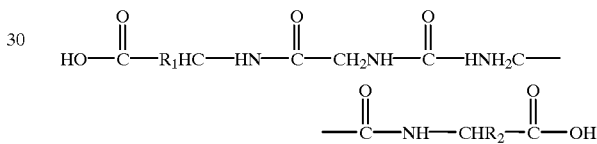

wherein $R_1$ and $R_2$ may be the same or different and represent the groups, including hydrogen, necessary to complete a dipeptide which includes any two of the twenty naturally occuring amino acids found in proteins. The invention is also considered to include such dipeptides composed of other non-toxic amino acids known in the art.

It is also an object of the invention to provide a method of detecting *Helicobacter pylori* infection comprising administering a composition of the invention to a subject and testing a biological sample from the subject for the presence of a diagnostic marker. This biological sample may be, for example, a blood sample or a urine sample.

It is a further object of the invention to provide method of delivering a therapeutic compound comprising administering a composition of the invention to the gastrointestinal tract of a subject infected with *Helicobacter pylori*.

The present invention has several major advantages over the prior art techniques of diagnosing the presence of *Helicobacter pylori* infection of the stomach or duodenum:

1. It is noninvasive and relatively inexpensive compared to the use of an endoscopic procedure to biopsy a sample of the stomach.

2. It has an advantage over serological antibody tests because it can detect active infections and determine the response to treatment (antibody based tests cannot reliably distinguish active infection from infection in the remote past).

3. It has an advantage over breath testing, because it does not require cumbersome equipment, special training of technicians or unwieldy instructions to be followed by the patient. For the present invention, a simple blood or urine sample is collected.

4. Blood or urine can be collected at the patient's convenience (even at home, in the case of urine samples) and stored for later analysis.

5. Some of the markers can be detected by simple, inexpensive and standard biochemical methods, readily available in any medical laboratory, as opposed to mass spectrometry and scintigraphy for the presently available breath tests.

DETAILED DESCRIPTION OF THE INVENTION

Three strategies are adopted to produce the urease-responsive delivery systems: 1) a microsphere, which contains a diagnostic marker or a therapeutic compound, is stabilized by an urease-sensitive crosslinker. The crosslinker is cleaved by urease, which then leads to the decomposition of the microsphere and the release of the diagnostic marker or the therapeutic compound; 2) dipeptides are coupled via their amino groups by an urea bond. In the presence of urease, the dimer is decomposed to yield a dipeptide; 3) a diagnostic marker or a therapeutic compound is covalently conjugated to the surface of a microsphere via an urease-sensitive bond. Release of the compounds is responsive to urease. The chemical schemes are described in details below.

1. Release from microspheres stabilized by an urease-sensitive crosslinker.

1.A. Synthesis of urease-sensitive crosslinker

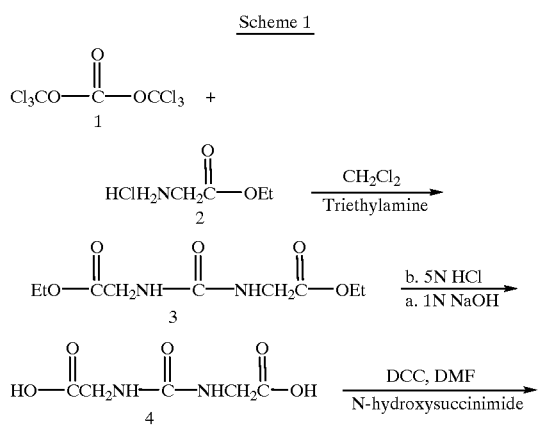

-continued

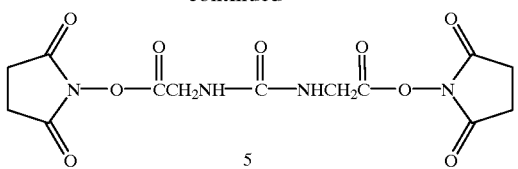

Synthesis of compound 3:

12.46 g (42 mmol) of triphosgene, 33.50 g (240 mmol) of glycine ethyl hydrochloride and 200 mL of dichloromethane were added to a flat-bottom flask. A mixture of 50 g (495 mmol) of triethylamine and 100 mL of dichloromethane was added into the stirred reaction system in an ice-salt bath over a period of 2 hours. After a further 5 min. of stirring while the ice-salt bath was removed, the reaction mixture was stirred for 10 min. at room temperature. A light yellowish solution was obtained and evaporated to dryness. The triethylamine hydrochloride salt was removed by washing the solid by 300 mL of cold water. The crude product was recrystallized from chloroform or ethyl acetate to yield 21.50 g of pure product (yield 77.23%). The chemical purity of the compound was verified by proton FT-NMR.

Synthesis of compound 4:

Into a 500 mL flat-bottom flask was added 21.50 g (92.67 mmol) of compound 3 and 50 mL of water and immersed in an ice bath. After 5 min., 200 ml of 1N sodium hydroxide was added. The reaction mixture was stirred for 1.5 hour, and then acidified with 5N hydrochloric acid to pH 2–3. The solid was isolated by filtration, washed with two 10-mL portions of ice-water, and lyophilized to produce 12.52 g of white solid (yield 76.76%). The chemical identity was confirmed by proton FT-NMR.

Synthesis of compound 5:

2.06 g of DCC(N, N'-dicyclohexyldiimide) (10 mmol) was added in one portion into a 50 mL flat-bottom flask charged with 0.75 g of compound 4 (4.25 mmol), 1.15 g of N-hydroxysuccinimide (10 mmol) and 10 mL of dimethylformide immersed in an ice bath. After stirring for 2.5 hours, the reaction mixture was stored overnight at 4° C. The dicyclohexyl urea was removed by filtration and washed with small quantity of DMF (10 mL). The product was then precipitated from solution by addition of about 400 mL of diethyl ether, removed by filtration and recrystallized from acetonitrile or acetone to yield 0.35 g of product (yield 22.14%). The structure of the product was characterized by proton FT-NMR.

1.B. Synthesis and enzymatic degradation of gelatin microspheres stabilized by urease-sensitive crosslinker (compound 5).

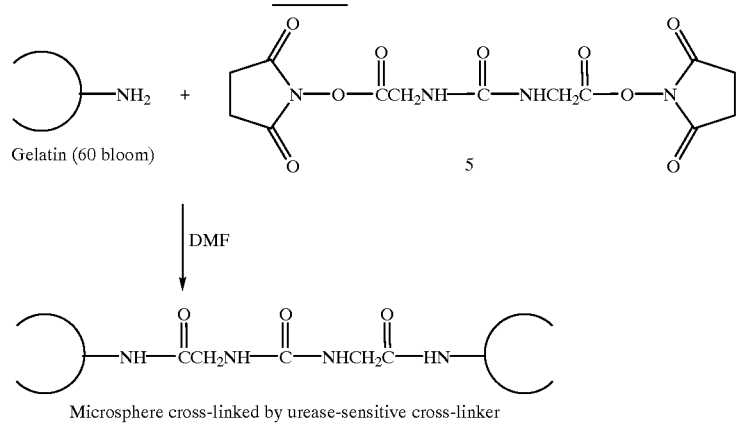

Microsphere cross-linked by urease-sensitive cross-linker

Ten mL of 4% gelatin PBS buffer (pH 8.50) solution (gelatin of 100 bloom dissolved in 0.1 M phosphate buffer) was sprayed into a liquid nitrogen bath. The frozen microspheres were immersed in 60 mL of dimethylformamide (DMF) cooled to −40° C. and containing 0.1 g of urease-sensitive cross-linker (compound 5). After the reaction was allowed to proceed for 25 min., the microspheres were collected by filtration, transferred into 40 mL of pre-cooled ethanol, and then kept overnight at 40° C. The microspheres were then isolated by filtration and further washed with cold ethanol. The microspheres were then placed in 5 mL of 1 U/mL urease PBS buffer (pH 7.0) solution. Over a period of 24 hours, the microspheres decomposed gradually as observed under a light microscope. In contrast, stabilized microspheres remain stable for weeks in the PBS solution in the absence of urease. The unique compound has a urea bond in the middle, and two very reactive functional groups at the two ends for crosslinking reaction.

2. Dimerization of amino acids by cross-linker 5 and the degradation of the dimer by urease (type III, Jack beans).

Synthesis of compound 1:

The solution of 0.50 g of glycine (2 mmol) dissolved in 10 mL of distilled water was adjusted to pH 8.50 using 1N sodium hydroxide and immersed in an ice bath. 0.37 g of cross-linker 5 (1 mmol) was added. The pH of the reaction solution was maintained at 8.0–9.0 until compound 5 totally dissolved. After further agitation for 5 min., the reaction mixture was acidified to pH 1.0 using 5 N HCl, and then stored for 1 hour in refrigerator (t=4° C). 0.15 g of solid was obtained by filtration. The chemical structure of the product was confirmed by proton FT-NMR.

Degradation of compound 1 by urease (type III, Jack beans):

Ten mg of compound 1 was dissolved in 5 mL of 1 U/mL urease PBS buffer (pH 7.0) solution. The mixture was kept for 20 hours at room temperature. Cleavage of the urea was confirmed by the ninhydrin assay, showed a strong absorbance at about 570 nm using the mixture of the same concentrated urease and ninhydrin solution as control (FIG. 1).

3. Conjugation of a diagnostic agent to the surface of microspheric carrier via a urease-sensitive bond.

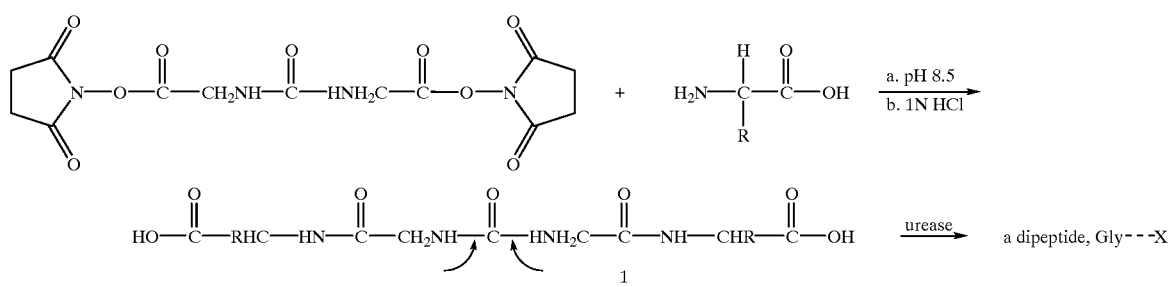

In this scheme, R represents, for example, a group which completes any naturally occuring amino acid. In this regard, both halves of the dimer need not be identical. The dipeptide should be a compound which is absorbed from the GI tract, is fairly nontoxic and which is stable and detectable in blood and preferably urine.

Scheme 3

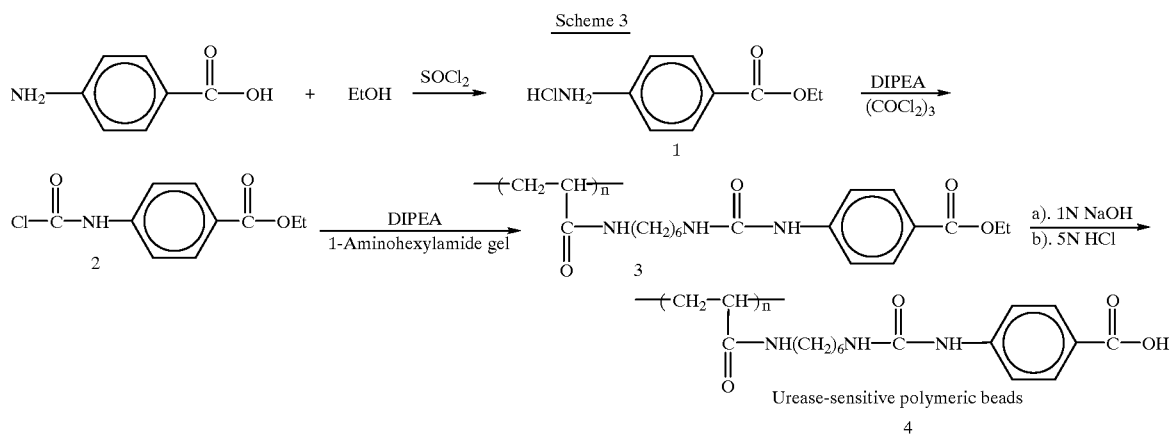

DIPEA: diisopropylethylamine
1-Aminohexylamide gel: poly(acrylic acid 6-aminohexylamide) beads 3.A. Synthesis of compound 1:

13.70 g (100 mmol) of para-aminobenzoic acid was suspended in 100 mL of anhydrous ethanol and immersed in an ice bath. The coupling agent thionyl chloride was added dropwise through an addition funnel. The solution was then stirred for 2 hours at room temperature and refluxed for about 4 hours (t≈80° C). The excess ethanol was removed by vacuum distillation. The crude product was recrystallized from ethanol to produce 18.50 g of white solid (yield 92.0%). The chemical structure was verified by proton FT-NMR.

3.B. Synthesis of compound 4:

To a solution of 2.08 g of triphosgene dissolved in 50 mL of dichloromethane immersed in an ice salt bath, the mixture of 4.0 g (20 mmol) of compound 1 and 5.2 g (40 mmol) of diisopropylethylamine (DIPEA) in 100 mL of dichloromethane was added dropwise over a period of 1.5–2.5 hours. After a futher stirring of 0.5 hour, a mixture of 2.58 g (20 mmol) of DIPEA and 1.70 g (10 mmol) of 1-aminohexylamide gel (beads) in 20 mL of dichloromethane was added. Stirring was continued overnight. The reaction mixture was concentrated to dryness and immersed in ice bath, and 100 mL of 1 N sodium hydroxide was then added. After stirring was continued for 3 hours, 5 N hydrochloric acid was added to bring the pH to 2–3. Beads were harvested by filtration and washed several times with large quantities of distilled water, then dried with lyophilization to yield 1.72 g of beads.

3.C. Release of para-aminobenzoic acid (PABA) in the presence of urease:

0.2 g of beads 4, 0.00323 g (100 U) of urease (type III, Jack bean) and 10 mL of 0.1M PBS buffer (pH 7.0) were charged into a 15 mL of centrifuge tube. The mixture was left standing overnight at room temperature. The degradation products were separated from the enzyme and the polymeric beads by extensive dialysis for 24 hours. The dialysate was concentrated to dryness. The residue was dissolved in 10 mL of PBS buffer (pH 7.0) for UV spectrophotometric analysis. An absorbance at about 275 nm showed that the enzymatic breakdown products was PABA.

Scheme 4

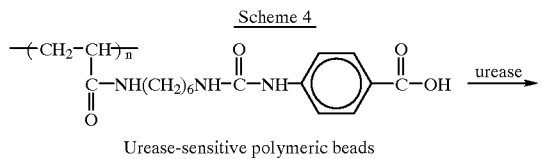

Urease-sensitive polymeric beads

4

-continued

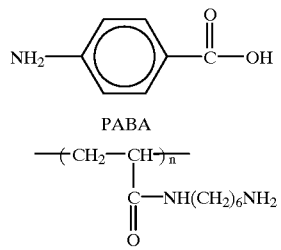

References cited herein are hereby incorporated by reference.

What is claimed is:

1. A composition for delivery of a diagnostic marker or a therapeutic compound, said composition comprising a microsphere stabilized by a cross-linker containing a urease sensitive bond, said cross-linker having the formula:

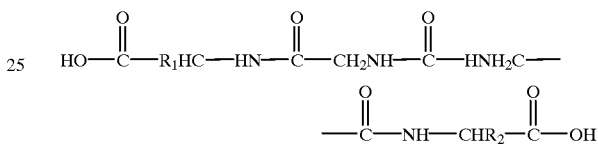

wherein $R_1$ and $R_2$ may be the same or different and represent the groups necessary to complete any naturally occurring amino acid.

2. The composition of claim 1 wherein said microsphere comprises gelatin.

3. The composition of claim 1 wherein said microsphere comprises poly(acrylic acid 6-aminohexylamide) beads and said diagnostic marker comprises p-aminobenzoic acid.

4. The composition of claim 1 wherein $R_1$ and $R_2$ are H.

5. The composition of claim 1 wherein said therapeutic compound is selected from the group consisting of omeprozole, amoxycillin, tetracycline and metronidazole.

* * * * *